United States Patent
Brachman et al.

(10) Patent No.: US 9,492,683 B2
(45) Date of Patent: Nov. 15, 2016

(54) DOSIMETRICALLY CUSTOMIZABLE BRACHYTHERAPY CARRIERS AND METHODS THEREOF IN THE TREATMENT OF TUMORS

(71) Applicant: GAMMATILE LLC, Gilbert, AZ (US)

(72) Inventors: David Brachman, Phoenix, AZ (US); Peter Nakaji, Phoenix, AZ (US); Heyoung McBride, Phoenix, AZ (US); Emad Youssef, Tempe, AZ (US); Theresa Thomas, Gilbert, AZ (US)

(73) Assignee: GammaTile LLC, Gilbert, AZ (US)

( * ) Notice: Subject to any disclaimer, the term of this patent is extended or adjusted under 35 U.S.C. 154(b) by 214 days.

(21) Appl. No.: 14/216,723

(22) Filed: Mar. 17, 2014

(65) Prior Publication Data
US 2014/0275715 A1 Sep. 18, 2014

Related U.S. Application Data

(60) Provisional application No. 61/800,983, filed on Mar. 15, 2013.

(51) Int. Cl.
*A61N 5/00* (2006.01)
*A61N 5/10* (2006.01)

(52) U.S. Cl.
CPC .......... *A61N 5/1007* (2013.01); *A61N 5/1015* (2013.01); *A61N 2005/1011* (2013.01); *A61N 2005/1024* (2013.01)

(58) Field of Classification Search
CPC ............. A61N 5/1001; A61N 5/1007; A61N 5/1014; A61N 2005/1011; A61N 2005/1012; A61N 2005/1024; A61N 2005/1087; A61N 2005/1089

USPC ......................................................... 600/1-8
See application file for complete search history.

(56) References Cited

U.S. PATENT DOCUMENTS

| | | | |
|---|---|---|---|
| D244,393 | S | 5/1977 | Collica et al. |
| 4,706,652 | A | 11/1987 | Horowitz |
| 4,754,745 | A | 7/1988 | Horowitz |
| 4,946,435 | A | 8/1990 | Suthanthiran et al. |
| 5,030,195 | A | 7/1991 | Nardi |

(Continued)

FOREIGN PATENT DOCUMENTS

| | | |
|---|---|---|
| DE | 613 528 | 5/1935 |
| EP | 0 906 769 A2 | 4/1999 |

(Continued)

OTHER PUBLICATIONS

Crepeau, R.H., et al., "Image Processing of Imperfect Protein Arrays: Sectioned Crystals and Tubulin Sheets and Rings". Elec. Microsc. Soc. Amer. Proc. 40:84-87, 1982.

(Continued)

*Primary Examiner* — John Lacyk
(74) *Attorney, Agent, or Firm* — Knobbe, Martens, Olson & Bear LLP

(57) ABSTRACT

Brachytherapy radioisotope carrier systems and methodology for providing real-time customized brachytherapy treatment to subjects with tumors difficult to control using conventional radiation therapy techniques. The invention generally relates to devices, methods and kits for providing customized radionuclide treatments, to help cure, slow progression or regrowth, or ameliorate the symptoms associated with tumors.

11 Claims, 10 Drawing Sheets

(56) References Cited

U.S. PATENT DOCUMENTS

| | | |
|---|---|---|
| D381,080 S | 7/1997 | Ohata |
| 5,772,574 A | 6/1998 | Nanko |
| 5,840,008 A * | 11/1998 | Klein .................. A61N 5/1002 600/3 |
| 5,871,708 A | 2/1999 | Park et al. |
| D408,957 S | 4/1999 | Sandor |
| 5,967,966 A | 10/1999 | Kronholz et al. |
| 5,997,842 A | 12/1999 | Chen |
| 6,017,482 A | 1/2000 | Anders et al. |
| D420,452 S | 2/2000 | Cardy |
| D420,745 S | 2/2000 | Cardy |
| D420,746 S | 2/2000 | Cardy |
| D443,061 S | 5/2001 | Bergstrom et al. |
| 6,248,057 B1 | 6/2001 | Mavity et al. |
| 6,385,477 B1 | 5/2002 | Werner et al. |
| 6,450,937 B1 | 9/2002 | Mercereau et al. |
| 6,512,943 B1 | 1/2003 | Kelcz |
| 6,712,508 B2 | 3/2004 | Nilsson et al. |
| D488,864 S | 4/2004 | Fago et al. |
| 6,787,042 B2 | 9/2004 | Bond et al. |
| D561,896 S | 2/2008 | Jones |
| D580,056 S | 11/2008 | Orthner |
| D580,057 S | 11/2008 | Ramadani |
| 8,039,790 B2 | 10/2011 | Cho et al. |
| D657,474 S | 4/2012 | Dona |
| D680,649 S | 4/2013 | Jagger et al. |
| D681,210 S | 4/2013 | Beiriger et al. |
| D681,812 S | 5/2013 | Farris et al. |
| D681,813 S | 5/2013 | Jagger et al. |
| D686,341 S | 7/2013 | Nakaji et al. |
| D686,744 S | 7/2013 | Nakaji et al. |
| D686,745 S | 7/2013 | Nakaji et al. |
| D686,746 S | 7/2013 | Nakaji et al. |
| D686,747 S | 7/2013 | Nakaji et al. |
| D686,748 S | 7/2013 | Nakaji et al. |
| D687,568 S | 8/2013 | Nakaji et al. |
| D687,966 S | 8/2013 | Nakaji et al. |
| D687,967 S | 8/2013 | Nakaji et al. |
| 8,600,130 B2 | 12/2013 | Eriksson Järliden |
| 8,605,966 B2 | 12/2013 | Eriksson Järliden |
| 8,825,136 B2 | 9/2014 | Giller et al. |
| 8,876,684 B1 | 11/2014 | Nakaji et al. |
| 8,939,881 B2 | 1/2015 | Nakaji et al. |
| 8,974,364 B1 | 3/2015 | Nakaji et al. |
| 9,022,915 B2 | 5/2015 | Nakaji et al. |
| 2001/0044567 A1 | 11/2001 | Zamora et al. |
| 2003/0088141 A1 | 5/2003 | Terwilliger et al. |
| 2003/0130573 A1 | 7/2003 | Yu et al. |
| 2004/0109823 A1 | 6/2004 | Kaplan |
| 2004/0116767 A1 | 6/2004 | Lebovic et al. |
| 2004/0242953 A1 | 12/2004 | Good |
| 2005/0035310 A1 | 2/2005 | Drobnik et al. |
| 2005/0244045 A1 | 11/2005 | Eriksson |
| 2006/0063962 A1 | 3/2006 | Drobnik et al. |
| 2006/0173236 A1 | 8/2006 | White et al. |
| 2007/0225544 A1 | 9/2007 | Vance et al. |
| 2008/0004714 A1 | 1/2008 | Lieberman |
| 2008/0221384 A1 | 9/2008 | Chi Sing et al. |
| 2009/0131735 A1 | 5/2009 | Drobnik et al. |
| 2009/0253950 A1 | 10/2009 | Rapach et al. |
| 2010/0056908 A1 | 3/2010 | Giller et al. |
| 2010/0200778 A1 | 8/2010 | Drobnik et al. |
| 2010/0228074 A1 | 9/2010 | Drobnik et al. |
| 2010/0268015 A1 | 10/2010 | Drobnik et al. |
| 2010/0288916 A1 | 11/2010 | Cho et al. |
| 2011/0013818 A1 | 1/2011 | Eriksson Järliden |
| 2011/0206252 A1 | 8/2011 | Eriksson Järliden |
| 2013/0131434 A1 | 5/2013 | Nakaji et al. |
| 2013/0338423 A1 | 12/2013 | Nakaji et al. |
| 2014/0316187 A1 | 10/2014 | Nakaji et al. |
| 2015/0057487 A1 | 2/2015 | Nakaji et al. |
| 2015/0196778 A1 | 7/2015 | Nakaji et al. |

FOREIGN PATENT DOCUMENTS

| | | |
|---|---|---|
| JP | H09-028810 | 4/1997 |
| JP | 2007-512112 | 5/2007 |
| JP | 2009-515603 | 4/2009 |
| JP | 2010-536529 | 12/2010 |
| WO | WO 2007/106531 A1 | 9/2007 |

OTHER PUBLICATIONS

Crepeau, R.H., et al., "Reconstruction of imperfectly ordered zinc-induced tubulin sheets using cross-correlation and real space averaging". Ultramicroscopy, 6, 7-18, 1981.

Nori, D., et al. Introperative brachytherapy using Gelfoam radioactive plaque implants for resected stage III non-small-cell lunch cancer with positive margin: A pilot stud. J. Surg ONcol. 60:257-261. 1995.

Hilaris, BS., et al. Intraoperative radiotherapy in stage I and II lunch cancer. Semin Surg. Oncol. 3:22-32. 1987.

Rivard, MJ., Brachytherapy dosimetry parameters calculated for 131 Cs source. Med Phys. 34(2): 754-765, 2007.

Hamilton, AJ., et al. The use of gold foil wrapping for radiation protection of the spinal cord for recurrent tumor therapy. Int. J. Radiat Oncol Bioi Phys. 32(2): 507-511, 1995.

Parashar, B. et al. Cesium-131 permanent see brachytherapy: Dosimetric evaluation and radiation exposure to surgeons, radiation oncologists, and staff. Brachytherapy. 10:508-511, 2011.

Huang, K. et al. Surgical resection and permanent iodine-125 brachytherapy for brain metastases. J. Neurooncol. 91: 83-93, 2009.

Rogers, CL., et al. Surgery and permanent 125-1 seed paraspinal brachytherapy for malignant tumors with spinal cord compression. Int. J. Radial Oncol Bioi Phys. 54(2): 505-513, 2002.

Dagnew, E., et al. Management of newly diagnosed single brain metastasis using resection and permanent iodine-125 seeds without initial whole-brain radiotherapy: a two institution experience. Neurosurg Focus. 15;22(3):E3, 2007.

Wernicke, AG., et al. Feasibility and safety of Gliasite brachytherapy in the treatment of CNS tumors following neurosurgical resection. J. Cancer Res Ther., Jan.-Mar. 2010, vol. 6—Issue 1, 65-74.

Murphy, MK, et al. Evaluation of the new cesim-131 seed for use in low-energy x-ray brachytherapy. Med Phy 31(6): 1529-1538, Jun. 2004.

Delaney, TF., et al. Intraoperative dural irradiation by customized 1921 ridium and 90Yttrium brachytherapy plaques. Int. J. Radiat Oncol Biol Phys. 57(1): 239-245, 2003.

Cole, Pd., et al. A comparative long-term assessment of four soft tissue supplements. Anesthetic Surg J. 31(6). 674-681, 2011.

Gutin, P.H., et al. Brachytherapy of recurrent tumors of the skull base and spine with iodine-125 sources. Neurosurgery 20:938-945, 1987.

Marchese, M.J., et al., A versatile permanent planar implant technique utilizing iodine-125 seeds imbedded in gelfoams. Int J. Radiat Oncol Biol Phys 10:747-751, 1984.

Patel, S., et al. Permanent Iodine-125 interstitial implants for the treatment of recurrent Glioblastoma Multiforme. Neurosurgery 46 (5) 1123-1128, 2000.

Gutin, P.H., et al. A coaxial catheter system for afterloading radioactive sources for the interstitial irradiation of brain tumors. Technical note. J. Neurosurg 56: 734-735, 1982.

Hilaris, B.S., et al. Interstitial irradiation for unresectable carcinoma of the lung. Ann Thoracic Surg 1975; 20:491-500.

Jenkins, H.P., et al. Clinical and experimental observations on the use of a gelatin sponge or foam. Surg 20: 124-132, 1946.

Kneschaurek, P. et al.: "Die Flabmethode Zur Intraoperativen Bestrahlung. Öthe Flab-Method for Introperative Radiation Therapy", Strahlentherapie and Oknologie, Uran Und Vogel, Muenchen, DE, vol. 171, No. 2; Feb. 1, 1995, pp. 61-69.

International Search Report; International Application No. PCT/US2012/035907, mailed on Sep. 26, 2012; 3 pages.

International Search Report; International Application No. PCT/US2012/035909, mailed on Aug. 30, 2012; 3 pages.

(56) References Cited

OTHER PUBLICATIONS

Office Action dated Apr. 2, 2015; European Patent Application No. 12724426.7; 5 pages.

Office Action dated Oct. 30, 2015; European Patent Application No. 12724426.7; 4 pages.

Office Action dated Feb. 9, 2016; Japanese Application No. 2014-508190; 5 pages including english translation.

* cited by examiner

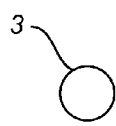
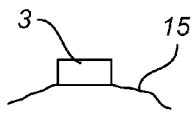
FIG. 3A    FIG. 3B
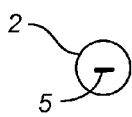
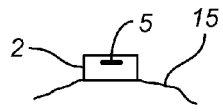
FIG. 3C    FIG. 3D
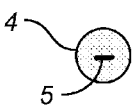
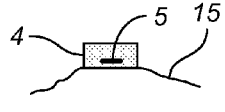
FIG. 3E    FIG. 3F
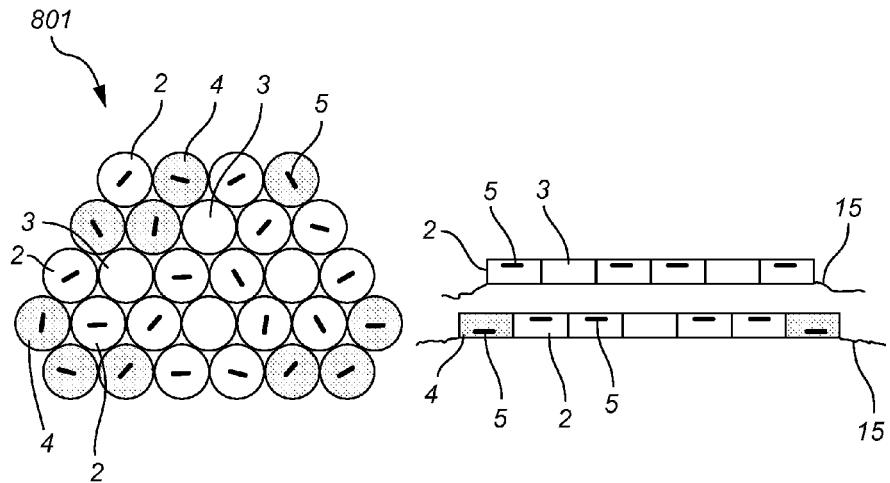
FIG. 3G

DOSIMETRICALLY CUSTOMIZABLE BRACHYTHERAPY CARRIERS AND METHODS THEREOF IN THE TREATMENT OF TUMORS

CROSS REFERENCE TO RELATED APPLICATION(S)

This application claims the benefit of priority under 35 U.S.C. §119(e) of U.S. Ser. No. 61/800,983, filed Mar. 15, 2013, the entire content of which is incorporated herein by reference.

BACKGROUND OF THE INVENTION

1. Field of the Invention

The invention generally relates to using radiation therapy to treat tumors and more specifically to dosimetrically customizable carriers kits and techniques for using the invention in the treatment of tumors.

2. Background Information

Tumors in living organisms are highly variable in size, location and their amount of infiltration into normal tissues, the variability of tumors in general make them very difficult to treat with a one-size fits all approach. Furthermore, the actual extent of tumors and/or void upon removal are typically not known precisely until presented in the operating room. Thus the options necessary to effectively treat a tumor or tumor bed need to be quite diverse.

Tumors are difficult to eradicate surgically as their infiltrative nature often precludes microscopically complete resection without undue morbidity or mortality. This local persistence of tumor cells may be controlled if sufficient radiation can be delivered safely prior to regrowth and replication of the residual tumor cells. Resective surgery, followed by radiation therapy in high doses, provides the best chance for local control of a tumor. However, the ability to deliver high doses of radiation in the post-operative setting is frequently limited by intolerance of surrounding healthy tissue. Radiation therapy is divided into external beam radiation therapy (EBRT) or teletherapy and internal radiation therapy or brachytherapy (BT). The therapeutic index is the relative amount of healthy tissue receiving high doses of radiation compared to the dose delivered to the tumor or tumor bed. Improving the therapeutic index may increase local control of tumors and/or decrease the morbidity of treatment. The inherently localized nature of BT is recognized as a technique to improve the therapeutic index in tumor treatment with radiation.

Brachytherapy involves placing a radiation source either into or immediately adjacent to a tumor. It provides an effective treatment of tumors of many body sites. Brachytherapy, as a component of multimodality cancer care, provides cost-effective treatment. Brachytherapy may be intracavitary, as in gynecologic malignancies; intraluminal, as in but not limited to esophageal or lung cancers; external surface, as in but not limited to cancers of the skin, or interstitial, as in but not limited to the treatment of various central nervous system tumors as well as extracranial tumors of the head and neck, lung, soft tissue, gynecologic sites, rectum, liver, prostate, and penis.

The currently available brachytherapy devices and techniques are lacking in the following areas: 1) the current carriers are unable to easily accommodate anatomically conformal and reproducible brachytherapy doses; 2) do not facilitate real-time dosimetric customization for sparing normal tissue, while delivering effective and safe doses of radiation to tumors; and 3) are not able to incorporate additional therapeutic agents, including chemotherapy, and viral, targeted, and DNA damage repair inhibitors.

The present invention addresses the deficiencies associated with current brachytherapy devices for treating highly variable tumors and tumor operative beds and comprises of novel brachytherapy radioisotope carrier systems and methodology for providing real-time customized brachytherapy treatment to patients with difficult to control tumors and tumor sites using conventional radiation therapy techniques.

SUMMARY OF THE INVENTION

The present invention generally relates to devices, methods and kits for providing a customized radionuclide treatment in a patient to help cure, slow progression or regrowth, or ameliorate symptoms associated with tumors. More specifically the embodiments described relate to a versatile dosimetrically customizable brachytherapy system for providing a targeted radiation dose to specific tissues on or within the human body using radionuclides in carriers.

An embodiment of the present invention comprises a radionuclide carrier system comprising of one or more individual implantable carriers configured to hold radioactive seeds in a precise location relative to a treatment area in order to produce a dosimetrically customizable implant in real-time for an area to be treated and wherein the individual carriers are small enough to fit in or on the area to be treated and the carriers are selected from one or more circular or gamma dot carriers and/or star or arm-based carriers. Additional carrier system embodiments may feature only one or more dot carriers or one or more star or arm-based carriers for delivering the radionuclide dose to the tissue of interest.

Embodiments of the invention comprise a radionuclide carrier system that is implantable and/or permanent (such as when used in the brain), while other embodiments include carrier systems that are temporary and/or not-implanted (such as when used to treat skin lesions and/or tumors).

An additional embodiment of a radionuclide carrier system is the customization and use of a real-time dosimetry based on precise dimensions and properties of the carriers to optimize the therapeutic index for an affected area. With additional embodiments including precise dimensions and properties of the carriers by utilizing gelatin-based or collagen-based biocompatible materials of differing thicknesses below and/or above a radiation source to act as a spacer to achieve a desired radiation dose delivery and a sparing of normal tissue.

Further embodiments of the radionuclide carrier system, relate to the asymmetrical placement of the radionuclide (seed) in the carrier which gives it additional inherent properties. In a normative location of the carrier the radionuclide source or seed is offset away from the tumor bed side more than it is from the "normal" tissue side (for example, in a 4 mm thick carrier, the radionuclide seed is 3 mm off tumor and 1 mm off "normal" tissue"). This may seem counterintuitive, but in practice the reasons are that; a) the normal side is usually a void, and b) if tissues on the void remain nearby, additional spacing material (sheets of collagen, cellulose, etc.) can be interposed. Additionally, the present invention also includes carrier systems which can be rapidly adjusted in real-time wherein one wants a localized dose increase, such as 1) a localized nodule of tumor remains just under one or more carriers, 2) a critical structure exists near or under the implant, such that a localized area of relatively lessened dose is desired, 3) that an implant consisting of a few to several carriers uniformly spaced has an inherently less radioactive periphery and more intensely radioactive center due to the inverse square law (similar to a charcoal grill at the edges and at the center), or 4) the implant area is quite small, and just a few carriers in the "normative" position would not deliver an adequate dose. In theses cases the embodied carrier system includes asymmetric source placement of carriers wherein in each case one or more individual carriers are reversed from the normative position (flipped) to solve the problem of hyper-local dose control. This is a 180 degree flip. If the usual (normative) orientation is thicker side toward tumor, then flipped is RFNO ('reversed from normative orientation'). Following the earlier example of a 4 mm thick carrier, the seed would be 3 mm off tumor and 1 mm off "normal" when in the normative location and 1 mm off tumor and 3 mm off "normal" when in the reversed from normative orientation.

Another additional embodiment achieves the real-time proper dosimetry by including a layer of tantalum, tungsten, titanium, gold, silver, or alloys of these or other high Z materials as a foil, grid or strip, internal to or on a surface of the carrier to facilitate sparing of normal tissue by diminishing the penetration of the radiation into adjacent normal tissues.

Additional embodiments include carriers manufactured as prefabricated carriers of various shapes and sizes; and some carriers may be preloaded "hot" with the radioactive seeds or "cold" in order to allow the radioactive seeds to be loaded with specifically desired seeds just prior to an implant procedure.

Further embodiments contemplate carriers which may be configured for the use of one or more low-energy radioactive seeds selected from Cs 131, Ir 192, I 125, Pd 103 or other isotopes used intra-operatively following surgical resection to form a permanent implant.

Yet further embodiments may include carriers with short range radioisotopes emitting beta or alpha particles.

Another embodiment of a carrier system comprises carrying additional therapeutic modalities including chemotherapeutic agents, viral treatments, targeted therapies, and/or DNA damage repair inhibitors. The carriers may further include a semi-permeable or impermeable membrane or other barrier capable of effecting a segregation of this material toward or away from tumor or normal tissues as may be desired.

Additional contemplated features of the carriers may include differential color coding to mark seeds with higher radiation strengths, differential thicknesses; indicator lines to allow a user to trim or shape a carrier as needed while maintaining the desired spacing for the calculated dosimetry; and visual and tactile indicators for a user to differentiate the tops from bottoms of carriers in the operating room/operative field and to maintain correct orientation and desired dosimetry.

A further additional embodiment for the carrier system comprises a atlas/program/spreadsheet/nomogram to guide a user in the planning of implants and to assist in ordering seeds/carriers based on preoperative shape, lesion size, location, histology and number of seeds needed. Such nomograms might include an atlas of pre-generated pictorial-type dosimetry maps of operative beds by size and shape as a guide to optimal real-time operative carrier placement and carrier orientation.

Another embodiment comprises a carrier system that is visible on CT and fluoroscopy, and/or is MRI compatible to allow the user to make accurate intra- and post-operative assessments. Additionally, radiofrequency identification (RFID) or other remote sensing positioning technology may be further used for intra and post-operative assessments.

Yet further embodiments of the present invention include inserting the individual implantable radionuclide carriers into or onto a tumor, a void remaining following resection, or a tumor bed; to help cure, slow progression or regrowth, or ameliorate symptoms associated with the tumor.

Additional embodiments of the radionuclide carrier system is for intraoperative permanent brachytherapy in treatment of various tumors of the body, including but not limited to tumors of the central nervous system, head and neck, soft tissues, bone, spine, lung, breast, skin, esophagus, stomach, liver, intestines, colon, rectum, prostate, pancreas, retroperitoneal space, kidney, bladder, pelvis, ovary, cervix, fallopian tubes, uterus and vagina.

BRIEF DESCRIPTION OF THE DRAWINGS

The principles of the present invention will be apparent with reference to the following drawings, in which like reference numerals denote like components:

FIG. 4 consists of FIG. 4A and FIG. 4B which are illustrations of dot based carriers attached to a three-dimensional structure wherein

DETAILED DESCRIPTION OF THE INVENTION

Figure 1A:
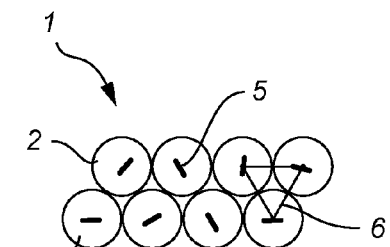
FIG. 1 consists of FIGS. 1A-1F which each show an illustration of dot based carriers in different configurations.

The present invention is based on the real-time selection and use of rapidly identifiable and conformable radionuclide carriers for providing an optimal dosimetric coverage of a tumor or tumor bed.

Definitions

For the purposes of the present invention Brachytherapy is defined as radiation treatment in which the source of the radiation is placed close to the surface of the body or within a natural or man-made cavity or space within the body a short distance from the area being treated.

For the purposes of the present invention Teletherapy is defined as radiation treatment in which the source of the radiation is at a distance from the body.

For the purposes of the present invention High Dose Rate is considered to be defined as the treatment with radiation doses above 12,000 cGy/hr.

For the purposes of the present invention Low Dose Rate is considered to be defined as the treatment with radiation in the dose range of 400-2000 cGy/hr.

For the purposes of the present invention High Z Materials are considered to be defined as any element with an atomic number greater than 20, or an alloy containing such materials.

For the purposes of the present invention the term Hot is considered to be a material that is Radioactive and the term Cold is considered to mean a material is low in radioactivity; or not radioactive.

For the purposes of the present invention Dosimetry is defined as the process of measurement and quantitative description of the radiation absorbed dose (rad) in a tissue or organ.

For the purposes of the present invention Real-time is defined as the moments or minutes during an operative procedure wherein the physician can fully visualize and specifically tailor a treatment approach to the exact anatomy and conditions found upon viewing a tumor or after surgical resection of a tumor that facilitates an optimal dosimetry in a precise manner.

For the purposes of the present invention Carrier is defined as a bio-compatible device with specific dimensions, both externally and internally, which functions to contain or carry and position a radioactive source (and possibly additional elements as needed). The carrier envisioned, by properties of design and construction, positions and fixes the location of the radioactive source internal to the individual carrier and simultaneously facilitates the rapid and precise combination of multiple carriers to form, when needed, an integrated multi-carrier structure for the safe and effective treatment of tumors.

For the purposes of the present invention a GammaDot or Dot carrier is defined as a type of radionuclide carrier that from the top looking down is round or almost round and that when single or multiple dots are placed in use to treat tumors the dots may surround or be placed within a three-dimensional structure or natural or man-made cavity and thus take on the overall shape of that which they are attached to.

For the purposes of the present invention a GammaStar or arm-based carrier is defined as a type of radionuclide carrier that assumes a conformable 3-dimensional shape when arranged and placed into an operative cavity or similar space and conforms to the treatment environment while maintaining the geometry necessary for an effective implant. However, in some embodiments the GammaStar or arm-based carrier may be used in its initial planar state to cover a relatively flat tumor or tumor bed area.

For the purposes of the present invention the Inverse Square Law applies to any entity which radiates out from a point in space. The equation is: Intensity=1/distance from the source squared (I=1/d2). With respect to Radiation, the law says if you double your distance from a source of ionizing radiation you will reduce the dose at the new distance by 4. It follows that if you reduce your distance from the source by half, it will increase the exposure to 4× the original value.

For the purposes of the present invention the term Interstitial is defined as pertaining to parts or interspaces of a tissue.

For the purposes of the present invention the term Operative Bed is defined as the void left after tissue removal and thus the area in need of treatment to help prevent the re-occurrence of tumors.

For the purposes of the present invention the term Tumor: is defined as an abnormal growth of tissue resulting from uncontrolled, progressive multiplication of cells; which can be benign or malignant.

For the purposes of the present invention the term Malignant is defined as tumors having the potential for or exhibiting the properties of anaplasia, invasiveness, and metastasis.

For the purposes of the present invention the term Cancer is defined as any malignant, cellular tumor.

For the purposes of the present invention the term Chemotherapy is defined as a cancer treatment method that uses chemical agents to inhibit or kill cancer cells.

Application of Embodied Carriers in "Real-Time"

In some applications, such as orthopedics or plastic reconstruction, the preoperative assessments and intraoperative findings can be very congruent. In contrast to these settings and despite medical advances, the precise location, exact extent and true configuration of a tumor remains largely unknown until an intra operative procedure. Current imaging technology is only capable of suggesting tumor vs. other types of tissue changes, and external imaging is particularly less useful in certain body areas (such as adjacent to highly vascular structures, and at the base of skull) as well as in situations where prior surgery or other treatments have distorted local anatomy. This problem is well established, and many tumor staging systems require the intraoperative assessment of a tumor as an essential part of the precise evaluation. Adding to and compounding this precise lack of anatomic information is that the operative bed, i.e. the void left after tissue removal (and thus the area in need of treatment to help prevent the re-occurrence of tumors) is often quite different from the shape and size of the anticipated cavity before the tumor was removed: in addition to the need for the removed tissue to be greater or smaller than that anticipated from preoperative studies, the nature of the tissues themselves, including elasticity, organ turgor pressure, and the tendency of any intra-corporeal space created to be rapidly reclaimed by previously displaced adjacent tissues makes a treatment that relies upon preplanning of precise dose control very difficult to successfully implement. Mortality and morbidity increase as operations lengthen, and the ability to rapidly and precisely adapt to the intraoperative findings is an essential component of any truly useful implant design. In this setting, real-time refers to moments to minutes, with the ability to make any substantive changes which are not just make do, but that result in optimal solutions in a precise manner which further yield better patient outcomes.

Further embodiments of the radionuclide carrier system, relate to the specific asymmetrical placement of the radionuclide (seed) in the carrier which gives the carrier additional inherent properties. Wherein, for example, the normative location of the source is 1) offset away from the tumor bed side more than it is from the "normal" tissue side (in a 4 mm thick carrier, it is 3 mm off tumor and 1 mm off "normal" tissue). This may be counterintuitive, but in practice is often the best way to do it because a) the normal side is usually a void, and b) if tissues are nearby, additional spacing material (sheets of collagen, cellulose, etc.) can be interposed. But in some other instances: once sometimes wants a localized dose increase, because either 1) a localized nodule of tumor remains just under one or more carriers, 2)

a critical structure exists near or under the implant, such that a localized area of relatively lessened dose is desired, 3) that an implant consisting of a few to several carriers uniformly spaced has an inherently less radioactive periphery and more intensely radioactive center due to the inverse square law (similar to a charcoal grill at the edges and at the center), or 3) the implant area is quite small, and just a few carriers in the "normative" position would not deliver an adequate dose. In these cases the embodied carrier system includes asymmetric source placement of carriers wherein in each case one or more individual carriers are reversed from the normative position (flipped) to solve the problem of hyper-local dose control. If the usual (normative) orientation is thicker side toward tumor, then flipped is RFNO ('reversed from normative orientation').

Application of Embodied Carriers in Central Nervous System Tumors

Despite meticulous surgical technique, tumors of the brain or spine often recur at or near the site of resection. This is because it is rarely feasible to resect these tumors with pathologically negative margins, especially in the more eloquent regions or where lesions are adjacent to vascular structures or nerves. Radiation therapy, utilizing an increasingly large variety of techniques, has been shown to be the single most effective adjuvant treatment to help prevent recurrence of central nervous system tumors. Interstitial brachytherapy combined with surgical resection of central nervous system tumors has been in use for several decades. Various types of radioactive sources are inserted under direct visualization during the surgery, as potentially more cost effective and less time-consuming therapy, without compromising outcomes.

Nevertheless, techniques for interstitial brachytherapy (BT) of central nervous system tumors have remained relatively crude. The brachytherapy device and methods embodied in the present invention improve the delivery of radiation by creating a carrier system to create combinations of carriers, dots and stars, each with radioactive sources contained within. These carriers, known as Dot carriers or "GammaDots" and "Star" or "Arm" carriers or "GammaStars" can be positioned to fit into operative beds by customizing them to the shape and size of individual operative cavities. The dots and stars can be tailored to protect sensitive normal structures, such as nerves or normal brain, while delivering desired high doses of radiation to the precise locations at highest risk of recurrence. The dots and stars may also be used as carriers for short-range radioisotopes emitting beta or alpha particles or for delivery of other therapeutic modalities, including chemotherapeutic agents, viral treatments, targeted therapies, and/or DNA damage repair inhibitors. They may also be designed to contain high Z materials and/or biocompatible spacers to afford significant directionality to the radiation treatment.

Application of Embodied Carriers Outside the Central Nervous System

Brachytherapy has been used to treat many tumors of extracranial sites such as head and neck, lung, soft tissue, gynecologic, rectum, prostate, penis, esophagus, pancreas and skin. Brachytherapy (BT) can be used alone or in combination with external beam radiotherapy and/or surgery. Patient outcomes are critically dependent upon proper patient selection and implantation technique. In general, patients with tumors that are intimately associated with critical normal structures to be preserved such as nerves, vessels, cosmetically apparent areas or visceral organs cannot be completely resected without undue morbidity or mortality. These tumors may be good candidates for BT performed in conjunction with surgical resection. Currently available techniques to produce the reliable source spacing needed for optimal geometry and subsequently radiation dosimetry, require catheters and shielding that are relatively bulky and therefore poorly conforming to the treated area. Consequently, they require considerable capital investment and the presence of a team of experts for effective use; and when preformed intraoperatively must be undertaken in a specially shielded operating room to avoid irradiation of adjacent staff and patients. These shortcomings limit the availability of these therapies to very few centers and compromise outcomes by decreasing tumor control and increasing complications from therapy. The brachytherapy device and methods contemplated in the present invention facilitates achieving optimal radioactive source arrangements for permanent low dose rate (LDR) BT in a user-friendly, readily available and cost-effective manner, by using a carrier system of geometrically customizable dot and/or arm-based/star carriers to contain radioactive sources to be placed into tumors or tumor beds.

Furthermore, the embodiments of the present invention also enables users to preferentially spare sensitive normal tissue without compromising the ability to deliver high dose radiation customized to both tumor and patient anatomy.

Additional embodiments of the dot and/or star carriers may include the ability of the carriers to deliver other cytotoxic agents, such as chemotherapy drugs or very short range radioactive sources such as Y-90 and alpha particles for placement directly into tumors, while maximally sparing normal tissue.

Illustrative embodiments of the invention are described below. In the interest of brevity, not all features of an actual implementation are described in this specification. It will, of course, be appreciated that in the development of any such actual embodiment, numerous implementation-specific decisions such as compliance with regulatory, system-related, and business-related constraints, which will vary from one implementation to another, must be made to achieve the specific goals. Moreover, such a developmental effort might be complex and time-consuming but with the benefit of this disclosure, would be a routine undertaking for those skilled in the art of radiation therapy.

Carrier Systems

Figure 9A:
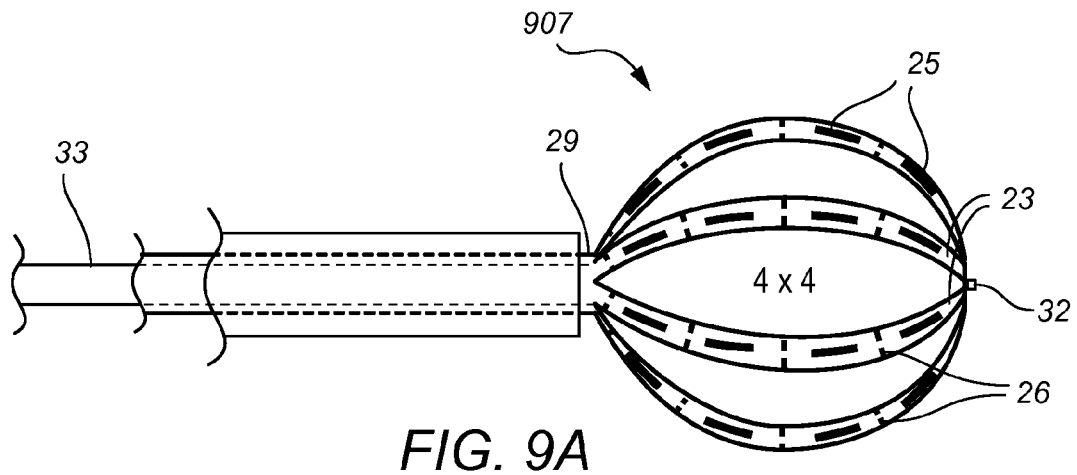
FIG. 9 consists of FIGS. 9A and 9B which show an illustration of two more arm-based carriers in a contracted, FIG. 9A, and expanded position, FIG. 9B.
Figure 9B:
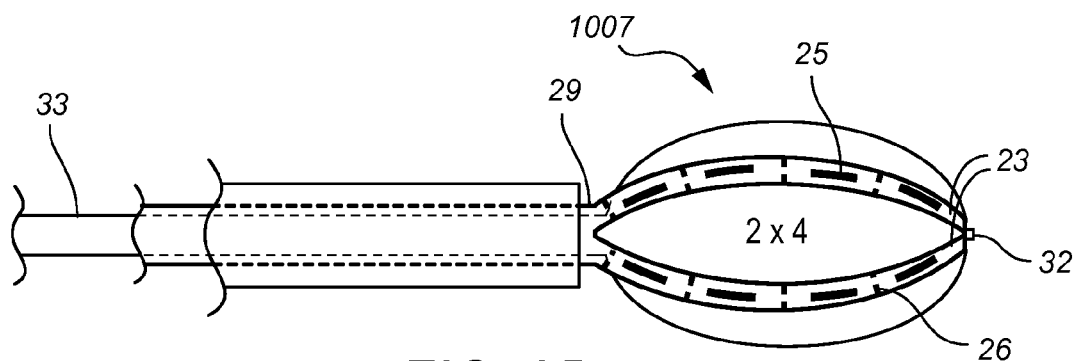
Figure 10:
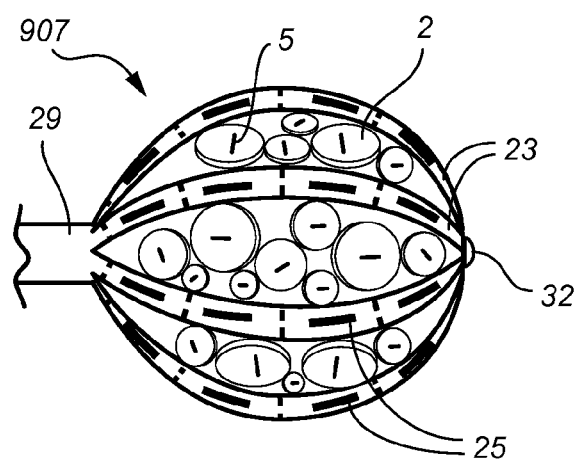
FIG. 10 is an illustration of another embodied carrier system wherein an arm-based carrier is combined with a plurality of dot based carriers, and fill space in a tumor bed.

Generally the carrier systems described herein and exemplified in FIGS. 1-10 involve the utilization of small individual or aggregated, implantable or superficial carriers in the form of dot type carriers (as shown in FIGS. 1-4) and stars or arm-based carrier systems (as shown in FIGS. 5-9) designed to be bearers of therapeutic agents such as radioactive seeds to produce a dosimetrically customizable carriers in real time for each patient and lesion. Additionally, a combination carrier system may include at least one star or arm based carrier in combination with one or more dot type carriers as shown in FIG. 10.

The carrier systems are designed to: create a carrier which allows for more precise and predictable dosimetry; an improved geometry with a better orientation of seeds to one another especially in the settings of real-time, intraoperative environments; is fully customizable to adjust to size/volume, location, and tumor type; and can provide differential dosing of tumor/tumor bed vs. normal tissues.

The carriers of differential thicknesses and set diameter are selected in real-time and the carriers may be marked, color coated or observable as having differential thicknesses of seed placement, so if user needed a seed 1 mm from operation bed they would choose a specific dot, if needed 2 mm choose a 2 mm specific dot if 3 mm could choose a 3 mm specific dot or flip a 4 mm thick dot wherein the seed is offset so that the seed is 1 mm or 3 mm from the operative bed depending on which side is towards the operative bed.

The carrier systems embodied are generally made of biocompatible materials known in the art and more specifically may be made of cellulose based or collagen based biocompatible materials.

The dot-based carriers may have different diameters to allow for a variety of spacing and sizing opportunities.

The general star or arm-based carrier designs include arms which are generally fixed by height, width and length, and set by need to maintain ideal implant geometry of seed spacing. The exact length and width depends upon the cavity size but the star carrier itself may be pre made and/or pre-sized. The arm or star based carrier additionally may have seed location presets. When the star or arm-based carrier material is in an expanded position or draped position around a three-dimensional support structure the arms and their seed placements offset to maintain seed spacing. The seed spacing contemplated may range from 5 mm to 15 mm, with 7.5 mm to 12.5 mm preferred, 8 mm to 12 mm more preferred and 10 mm a most preferred seed spacing interval between seeds.

The present invention also may include the use of a small implantable individual carriers constructed for the localized delivery of radioactive materials such as gamma or beta irradiation or alpha particles along with chemotherapy agents or tumoricidal/targeted/immunotherapeutic or viral/viral vector agent(s) on the side(s) of the carrier(s) adjacent to the tumor.

The present invention also may include the use of a small implantable individual carrier constructed for the localized delivery of radioactive materials such as gamma or beta irradiation or alpha particles along with radiation sensitizing agents and/or radiation damage repair inhibitors on the side(s) of the carrier(s) adjacent to the tumor.

The present invention also may include the use of a small implantable individual carrier constructed for the localized delivery of radioactive materials such as gamma or beta irradiation or alpha particles along with radiation protection compounds on the side(s) of the carrier(s) antipodal to the radiation source and/or tissue growth promotion/healing factor compounds on the side(s) of the carrier(s) antipodal to the radiation source.

The dot or star based carriers in the present invention include the adaptability of the carrier system to be isotope specific and manage the radionuclide strength and exposure to users and normal (non-targeted) tissues with a variety of measures including differential thicknesses as shown above, shielding materials, or spacing facilitators to place radiolabeled seeds in best place in regards to treatment of target and non-treatment of non-target.

The carriers may be MRI compatible and/or visible on fluoroscopy, radiofrequency identification (RFID), and CT, to facilitate accurate intra- and post-operative assessment.

The small individual implantable dots and arm or star carriers are designed to be carriers for radioactive seeds used to produce a dosimetrically customizable implant in real time for each patient and tumor.

The present invention may use a variation of seeds in any carrier (dot or star/arm type carrier) in order to provide the best dosimetry for the patient, tumor and space. The carriers may include one or more of the same seeds or various combinations of well-known low energy radioactive seeds such as Cs 131, Ir 192, I 125, Pd 103 or others commonly known in the art. The seeds placed within the carriers are generally placed as a therapeutic agent in the form of permanent implants intra-operatively following surgical resection, but there may be instance where implants are interchanged removed or replaced.

In other contemplated radionuclide carriers the carrier may include an "up" or "top" designation on the side opposite of the target zone surface. In instances wherein a dot-based carrier is used, a marking system associated with identifying whether the carrier is in the normative or non-normative position may be present. This marking or identification system may be done with any indicator, color coding or textural indicators to alert the user as to what position the carrier is in.

Application and Treatment with Customized Radionuclide Carrier Systems

The specialized carriers of the present invention provide for certain precise dimensions to allow the carriers to guide users (neurosurgeons, cardiothoracic surgeons, general surgeons, dermatologists, radiation oncologists, urological surgeons, veterinarians or other qualified providers) in maintaining precise and preplanned dosimetry needed to produce effective and safe outcomes.

The dosimetrically customizable implants of the present invention may be used as a means of treating, curing, ameliorating, or slowing the progression of various tumors of the body, including but not limited to; tumors of the central nervous system, head and neck, spine, soft tissues, bone, liver, lung, breast, skin, esophagus, stomach, intestines, colon, rectum, prostate, pancreas, retroperitoneal space, kidney, bladder, pelvis, ovary, cervix, fallopian tubes, uterus, and vagina.

The embodied carrier systems may be used in methods to facilitate intracavitary, intraluminal, interstitial, and external surface brachytherapy used with and without surgical resection of the tumors.

The embodied carrier systems may be used in methods specifically for treating extracranial, interstitial, intra-cavitary, surface or visceral site irradiation treatment of various primary and metastatic tumors.

The custom radionuclide carrier systems of the present invention may be used for implantation within the central nervous system and include a radiolabeled implant for interstitial implantation comprising a substantially rigid implantable matrix design to be a carrier for radioactive seeds to produce a dosimetrically customizable implant in real-time for each patient and lesion. Additional carrier systems contemplated are used for superficial or topical treatment of tumors and/or lesions most often in the skin.

The dosimetrically customizable carriers described herein may be used to treat, cure ameliorate or slow-down the progression and thus provide a defense against various brain tumors including but not limited to, meningioma, glioma, metastatic cancer and craniopharyngioma.

The types of tumors to be treated include primary, secondary and recurrent tumors involving the central nervous system.

A atlas/program/spreadsheet/nomogram to guide planning implants and ordering of seeds and carriers based on preoperative lesion size, shape, location, histology and number may be provided to assist the user when using the present carrier systems. A similar program/spreadsheet is also contemplated when carriers are not implanted but are applied to a set body area such as the skin.

This invention would also be useful in veterinary oncology, either alone or in combination with surgery. Fractionated radiation therapy is logistically more difficult and costly in animals, which require anesthesia prior to delivery of each fraction. Customizable BT, utilizing this invention, will enable delivery of effective and efficient treatment in properly selected tumors.

Hot-Dot Carrier Embodiments

Some of the general features of the Hot-Dot type carrier are listed below:

1) Round or almost round insures easy conformity to flat or curved surface.

2) Implant can be constructed quickly using series of round carriers, of single or multiple sizes.

3) Round or nearly round insures stable geometry: just apply with edges touching, so center to center distance (geometry) is predictable (always diameter dot a+ diameter dot b/2).

4) When geometry is predictable, dosimetry (radiation dose distribution in tissue) is able to be accurately calculated, either before surgery or intraoperatively.

5) Cold dots of same size can be used as spacers to maintain geometry and avoid too many "hot dots" so lessening chance of uneven dose/hot spots/overdose.

6) Supplied as individual dots, strands of dots, or packs.

7) Trim as needed between dots and trim individual dots to fit.

8) The location of internally placed seed(s) is/are marked on surface so as to allow trimming without disrupting integrity of internal source(s).

9) Biocompatible material, sized from about 5 mm to 20 mm (hot or cold) in diameter and thickness from about 1 to 8 mm, and general 2-5 mm.

FIGS. 1-4 show various exemplifications of carrier devices in dot form embodied in the present invention.

Figure 2A:
FIG. 2 consists of FIGS. 2A-2M which each show an illustration of mixed dot based carrier configurations.
Figure 2B:
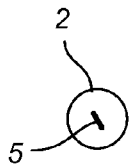
Figure 2C:
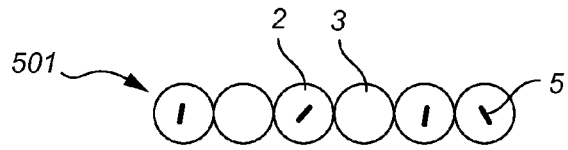
Figure 2D:
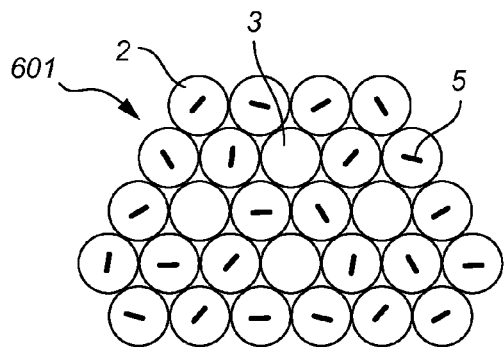
Figure 2E:
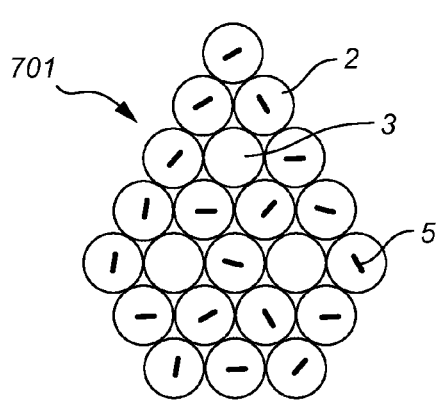
Figure 2F:
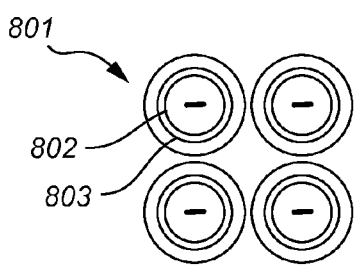
Figures 2H, 2I:
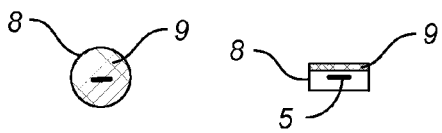
Figure 2G:
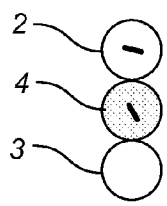
Figures 2J, 2K:
Figures 2L, 2M:
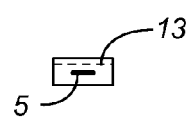
Figure 3L:
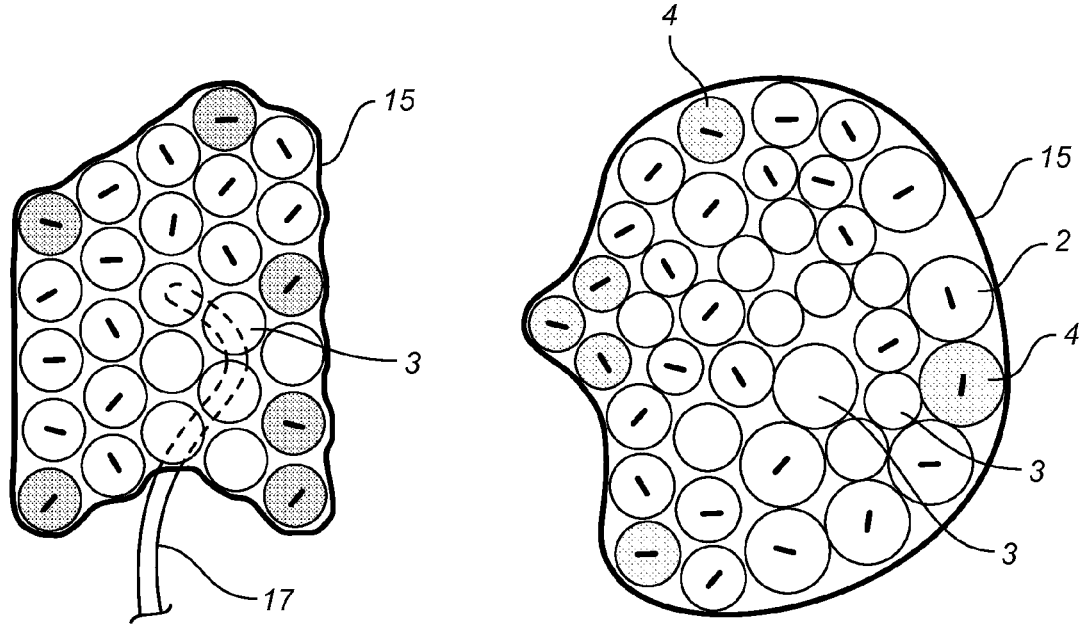
FIG. 3 consists of FIGS. 3A-3L which each show an illustration of dot based carriers in relation to a tumor bed.
Figure 3L:
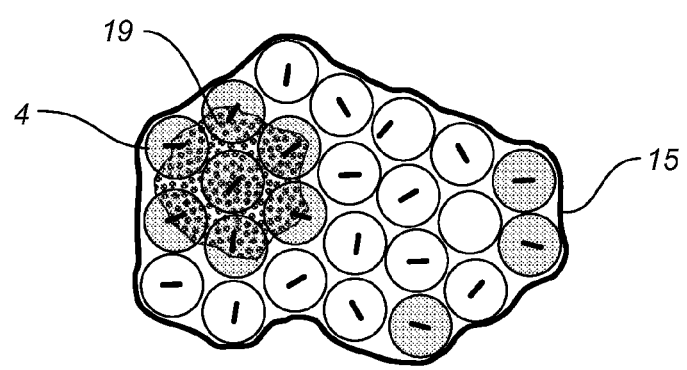

FIGS. 1-3 illustrate the multiple configurations possible with the dot-based system. Additionally, the round design where all of the edges touch allows and insures equal spacing. "Cold Dots" do not contain isotope are used to maintain geometry and/or dosimetry and/or structural integrity. Too many "hot dots" can cause too much radiation dose in certain areas, so blanks can be interspersed to lessen the local dose and/or the overall dose as desired.

Additionally, the collection of dots could be preloaded hot or in a pattern of hot and cold and excess hot dots could be just punched out as necessary to insure the correct dosimetry and/or placement is achieved. In FIG. 1 there are strands of "hot dots" which are shown as the dots with seed indicators. In FIG. 2 "Cold dots" are shown as blank dots without a seed indicator line and are used to create the spacing and dosimetry desired.

The embodied carriers are constructed using differential thicknesses of biocompatible materials below and/or above the radiation sources (as shown in FIG. 3) to achieve differential radiation dose delivery with relative sparing of normal tissue along with the use of a layer of tantalum, tungsten, titanium, gold, silver, or alloys of these or other high Z materials on the antipodal aspect (side away from the tumor) or internal to the carriers to provide sparing of normal tissue in portions of the body such as the brain and anywhere there is very limited physical space.

The present carriers may include the use of differential color codes to mark seeds with higher radiation strength or carrier thickness to tumor bed for improved radiation dose distribution for use with limited size and irregular shape targets.

Additional carriers may also have an impermeable membrane, bio-compound, high Z material or other barrier, which acts to prevent or impede the migration of the compound(s) or agents from the side(s) of the carrier(s) adjacent to the resected tumor to the antipodal side(s) of the carrier(s) (adjacent to normal tissue) and vice versa to create a differential therapeutic impact on the operative bed vs. adjacent tissues.

Additional carriers may use differential thickness of tissue equivalent material below and/or above the dots or stars and/or a construction of differing high Z materials to achieve the desired radiation dose delivery or normal tissue sparing targeting.

Although single dots may be utilized in the dot-based carrier systems, an advantage of the system is the ability to combine elements (dots) in real time to deliver a relatively uniform radiation dose to a user-defined area, without having to know or specify ahead of time the exact or near-exact dimensions of the intended treatment area. Prior systems have not been able to accomplish this degree of specificity in a permanent implant (no need to remove) or not without essentially direct contact of the radioactive sources with the tissue, a situation that can be extremely injurious. The present embodiments use source(s) within a 3 dimensional physical biocompatible carrier(s) of precise dimensions, along with non-source-containing carriers of comparable dimensions and construction. This allows the user to combine the elements quickly and easily in real time to produce the user-specified radiation dose distributions (dosimetry) desired. Because the location (depth top to bottom) of the source in a carrier is asymmetrical but the other dimensions are symmetric the carrier can be utilized in either a nominal or reversed (flipped) manner. Either position interposes sufficient material between the source and tissue to prevent direct source-to-tissue contact, thereby lessening the chance of direct tissue injury by radiation overdose. The Inverse Square Law applies to any entity which radiates out from a point in space. The equation is: Intensity=1/distance from the source squared (I=1/d2). With respect to Radiation, the law says if you double your distance from a source of ionizing radiation you will reduce the dose at the new distance by 4. It follows that if you reduce your distance from the source by half, it will increase the exposure to 4× the original value.

The nominal position envisioned creates ~2× the distance to tumor bed than the reversed/flipped position, resulting in a 94 percent difference in the surface radiation dose between the two orientations. This inherent design feature not only allows for a more uniform dose at depth than direct/near direct contact by the source to the treatment area but also creates a significant ability to manipulate a localized dose increase (e.g. over a nodule of residual tumor see FIG. 3L) or at the edges of a multi-dot carrier implant where the radiation dose is low because of the inherent physics of radiation (inverse square law). In addition, the placement of otherwise dimensionally identical but non-radioactive dots as spacers allows the user to take advantage of these same physics principals to lessen dose to critical structures within or near the operative bed, and/or increase the uniformity of the overall dose within the treatment area. These features, coupled with the stable geometry that round or functionally round carriers enforce when placed edge-to-edge allow rapid and predictable radiation dose distributions to be calculated using standard formulas for almost any final configuration devised.

The dots may be supplied as sheets of sources in biocompatible material with concentric circles about each source and marked with 6 mm and 8 mm and 10 mm and 12 mm and 14 mm or similar concentric rings (as FIG. 2F), and punch tool to be used to "cut" these from the sheet as needed in the desired size(s) and number. These can be "hot" or "cold", with the latter to function as spacers in multi-carrier implants.

It is envisioned that the variety of sizes available in the above contemplation will facilitate by allowing the user to place sources in smaller or within larger operative areas with greater flexibility.

Figure 1B:
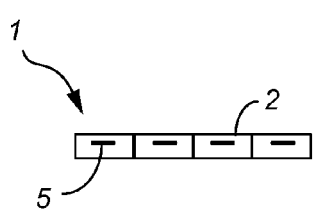

FIG. 1 consists of FIGS. 1A-1F which provides illustrations of contemplated dot based carriers in different configurations. FIG. 1A shows a dot based carrier 1 with a combination of eight hot dots 2 dispersed in two rows of four dot carriers. The seed indicator lines 5 in each dot carrier 2 are for illustration purposes only, and are meant to show first that the dot carrier 2 is a hot carrier loaded with a radioactive seed, and that the seed is located near the seed indicator line 5. FIG. 1B shows the same dot based carrier 1 shown in FIG. 1A from a side view in which the depth of the seed within each dot carrier 2 is indicated with seed indicator lines 5.

Figure 1C:
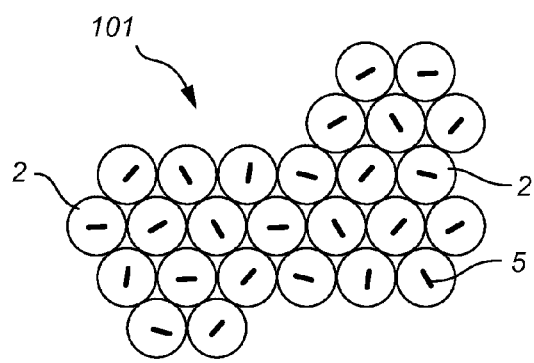

FIG. 1C, demonstrates another grouping 101 of dot carriers 2, in this carrier grouping 101 there are six rows of hot dot based carriers 2, but the rows are not uniform in length. The seed indicator lines 5 represent that each dot based carrier 2 is loaded and hot. The carrier systems 101 may be further trimmed by removing some of the dots 2 to fit within the tumor or tumor bed 15 (not shown).

Figure 1D:
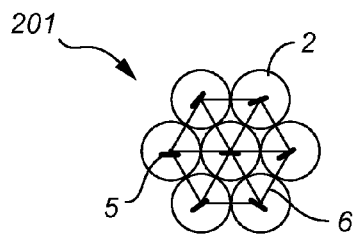
Figure 1E:
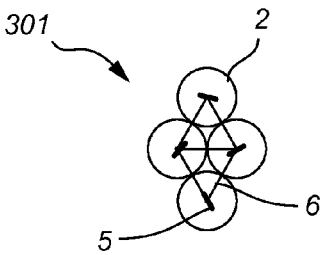

FIG. 1D and FIG. 1E, demonstrates two more groupings 201 and 301 of hot dot carriers 2 organized in a symmetrical grouping 201 of seven hot dot carriers 2 as shown in FIG. 1D or four hot dot 2 carriers shown in the dot grouping 301 of FIG. 1E. Additionally, each dot 2 is indicated as hot based on the seed indicator lines 5 present. The close relationship of all the hot dots demonstrated by the interconnected seed indicator line 6 represents a grouping of hot dots to produce a strong radionuclide dose.

Figure 1F:
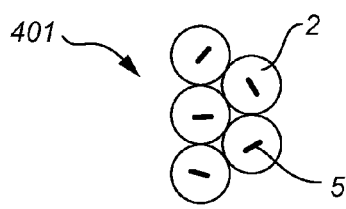

FIG. 1F demonstrates another grouping 401 of hot dot carriers 2 this time in a staggered or asymmetrical grouping 401 of five dot based carriers, with seed indicator lines 5 representing the dots as hot.

FIG. 2 consists of FIGS. 2A-2M which each provides an illustration of a mixed dot based carrier configuration. FIG. 2A is a single dot 3 based carrier but because it does not show a seed indicator line 5, it is a blank or cold dot 3 which are used for spacing and managing the dosimetry demands found in the operative field 15 (not shown). FIG. 2B is a hot single dot 2 based carrier with a seed indicator line 5. FIG. 2C shows a strip 501 of dot based carriers wherein some of the dots are hot 2 and some are cold 3. The dots may be manufactured in strips 501 or in any combination of groupings and trimmed and pieced together at time of use. FIGS. 2D and 2E demonstrate two more groupings of hot and cold dots 601 and 701.

FIG. 2F illustrates a grouping of hot dots 802 formed in a sheet 801 with illustrated concentric circles 803 surrounding the seed indicator line 805 which may be customized at time of use by punching out the desired sized dots with a punch out tool and placing the different size dots in accordance with the dosimetric demands of the tumor or tumor bed.

FIG. 2G illustrates the grouping of dot based carriers showing three different doses associated with the dot based carriers, the blank dot 3 is once again representative of an unloaded cold dot 3, and the hot dot carrier 2 with the seed indicator line 5 and otherwise blank is representative of a hot dot 2 in a normative position. The third gray dot 4 represents a hot dot such as hot dot 2 but wherein the dot 2 is flipped into a non-normative position 4 resulting in a higher radionuclide dose provided to the tumor or tumor bed.

FIG. 2H represents a top view of another hot dot 8 which additionally includes top surface shielding 9 with a high Z material. FIG. 2I illustrates a side view of the dot 8 of FIG. 2H and shows the relation of the surface shielding 9 compared to the seed location 5.

FIGS. 2J and 2K demonstrate a hot dot carrier 10 that comprises interior shielding 11 within the dot carrier 10 with a high Z material. FIG. 2J shows the top view and FIG. 2K illustrates a side view of the dot 10 of FIG. 2J and shows the relation of the interior shielding 11 compared to the seed location 5.

FIGS. 2L and 2M demonstrate a hot dot carrier 12 that further comprises an internal membrane or biologically active material 13 such as a DNA damage promoter or inhibitor, or a target agent within the dot carrier 12. FIG. 2L shows the top view and FIG. 2M illustrates a side view of the dot 12 of FIG. 2L and shows the relation of the internal membrane 13 compared to the seed location 5.

FIG. 3 consists of FIGS. 3A-3L which each provides an illustration of dot based carriers in relation to a tumor bed 15. FIG. 3A demonstrates a top view of a cold dot 3, and FIG. 3B illustrates a side view of the cold dot 3 of FIG. 3A placed on a tumor bed 15. FIG. 3C demonstrates a top view of a hot dot 2, and FIG. 3D illustrates a side view of the hot dot 2 of FIG. 3D placed on a tumor bed 15 wherein the respective seed placement 15 is viewable. FIG. 3E demonstrates a top view of a hot dot 2 that has been flipped into the hotter non-normative position 4, and FIG. 3F illustrates a side view of the non-normative dot 4 of FIG. 3E placed on a tumor bed 15 wherein the respective seed placement 5 is viewable.

FIG. 3G demonstrates an exemplary grouping of dot based carriers 801 placed in an operative or tumor bed 15 which consists of normative 2 and non-normative 4 placed hot dots and cold dots 3 used as dosimetric spacers. FIG. 3H demonstrates a side view of the third row from the top of the dot based carrier grouping 801 of FIG. 3G wherein each of the dots are cold 3 or hot 4 carriers in their normative position, whereas FIG. 3I demonstrates a side view of the fourth row from the top of the same carrier 801 and displays the relative seed locations 5 when the dots on the ends are flipped into non-normative positions 4, as compared to the internal hot 2 and cold dots 3.

FIG. 3J demonstrates another application or grouping of dot based carriers in an operative field 15. In this case non-normative hotter dots 4 are found along the periphery of the bed 15 and a grouping of cold dots 3 is placed around a anatomy to be shielded 15 such as a vessel or nerve that is chosen in real-time to not be radiated. If this vessel or nerve 15 shown were above the implant grouping, the cold dots 3 could be replaced by shielded hot dots 9 and still deliver the intended dose to the underlying operative bed (not shown).

FIG. 3K demonstrates another application or grouping of dot based carriers in an operative bed 15, but in this case the dots 2, 3, 4 are selected of various sizes and types to fill the field and maintain dosimetric spacing.

FIG. 3L demonstrates yet another application or grouping of dot based carriers, in this specific example a grouping of dot carriers are flipped in the non-normative position 4 and thus producing a localized "hotter" area placed over an area of particular concern 19 for tumor regrowth such as a nodule of tissues 19 unable to be surgically resected.

Figure 4A:
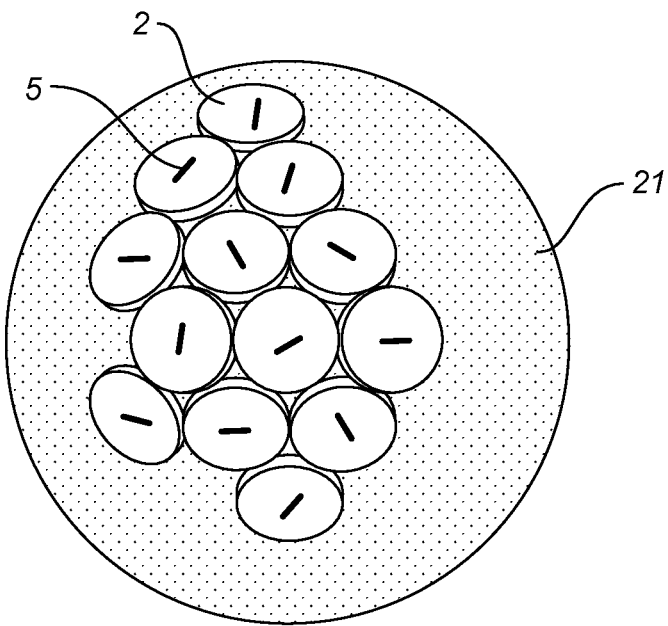
Figure 4B:
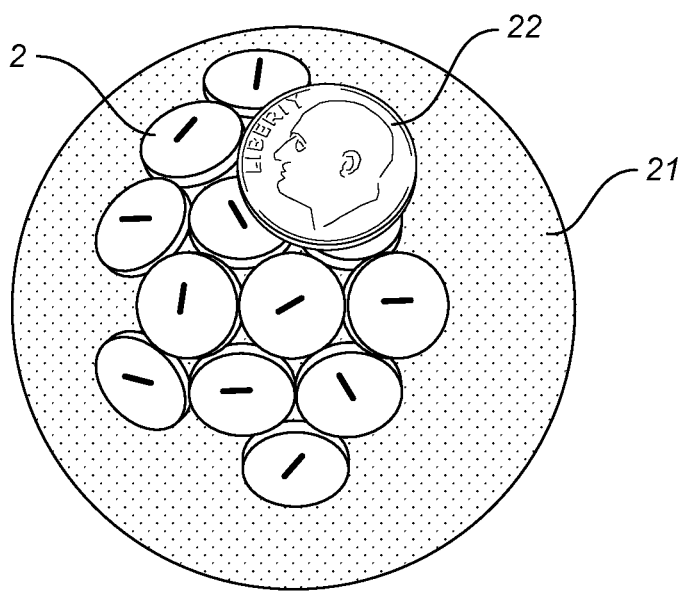
FIG. 4B shows a dime inserted for scale purposes.

FIG. 4 consists of FIG. 4A and FIG. 4B which are illustrations of hot dot 2 based carriers surrounding or draping a three dimensional structure 21 and thus taking on the shape of the structure 21 they are attached to. FIG. 4B with the added dime 22 gives a general scale of the dots 2 embodied in the present invention.

Arm-Based or Star Style Carriers Embodiment

FIGS. 5-10 show various exemplifications of carrier devices in star or arm based form embodied in the present invention.

Some of the general features of the Gamma Star type carrier are listed below:

1) Design insures easy conformity to spherical or elliptical cavities.

2) Design accommodates symmetrical or asymmetrical cavities.

3) Cavity may have either regular or irregular surface.

4) Cavity may be open ended or closed ended.

5) Pre-loaded Stars ("hot") or Stars loaded on site ("cold") conceived.

6) Designed such that implant can be completed quickly using preformed carriers of adjustable size thereby minimizing radiation exposure to users and staff.

7) "Size" refers to both a) arm number and b) arm length (see diagrams).

8) Designed with 3-8 "arms", at intervals of 120 degrees (3 arm star shown in FIG. 5A), 90 degrees (4 arm star shown in FIG. 5B), 72 degrees (5 arm star shown in FIG. 5C), 60 degrees (6 arm star shown in FIG. 5D), 51.5 degrees (7 arm star not shown), and 45 degrees (8 arm star shown in FIG. 5E) or similar to achieve desired function.

9) Arm length can be symmetrically shortened (e.g., to fit a smaller cavity) and to alter the source number (e.g., thereby altering dose).

10) Arm length can be asymmetrically shortened (e.g. to fit an asymmetrical cavity) and to alter the source number (e.g., thereby altering dose).

11) Arms can be selectively amputated (e.g., to adapt a 6 arm Star to form a 3 arm star) and to alter the source number (e.g., thereby altering dose).

12) May be constructed of individual arms, of various lengths, either supplied hot or cold.

13) Can be inserted free hand, robotically, endoscopically, or over a balloon-tipped or other expandable catheter.

14) May have an opening or other embodiment at intersection of arms to allow positioning over a catheter or other carrier/introducer.

15) May have additional openings at intervals along the arms to act as an aid in positioning and alignment.

16) May have markings at intervals in standard measures of distance to allow translation of surgical cavity or bed dimensions from direct observation, sounding with probes, ultrasound, CT, MRI or similar to aid in selecting or trimming to the proper size prior to placement. These same openings may act as trim indicators for maintaining a set geometry and thus radiation dosimetry.

17) Radiation source may be sealed isotopic sources (I 125, Pd 103, Cs 131, Ir 192, or similar), or another compatible unsealed isotopes (Ra 223, Y 90, or similar).

18) Seeds or similar fixed sources would be arranged at set locations along the arms consistent with obtaining uniform dosimetric coverage.

19) Temporary or permanent implantation of a biocompatible material wherein the arm length is from 20 mm to 100 mm; arm width is from 2 mm to 10 mm; and arm thicknesses from about 1 mm to 5 mm.

20) The arms may include a cold "tail" to allow endoscopic or other placement and subsequent manipulation or repositioning.

21) Arms may be open or gathered or attached to one another at distal ends to facilitate manipulation and placement.

One problem associated surgeons and oncologists often face when treating a subject include a subject with spherical and semispherical intracranial lesions which are common and thus so are similarly shaped postoperative cavities. Any useful carrier and coverage will need to adapt to this shape while being able to be implanted into the brain or other tissues, and still maintain "ideal" or nearly ideal geometry. One solution embodied by the present invention includes the creation of carriers, that when loaded with seeds and placed in the cavity conform to the three-dimensional environment while maintaining geometry of implant. In addition to the three-dimensional nature of the carrier, the carrier may possess additional possible properties previously mentioned including spacing function, differential thickness, and the possibility of combining with high-z materials for radiation protection. These carriers may also be designed so as to be compatible with placement of adjacent dots as needed for additional intraoperative flexibility.

Additionally the arm type carrier may be pre-manufactured in specific dimensions and available in a variety of sizes and/or capable of being trimmed to make smaller or combined to make bigger at time of use. The dimensions decided upon can be customized by the user based upon the tumor/cavity size and characteristics to achieve the necessary geometry.

Figure 5A:
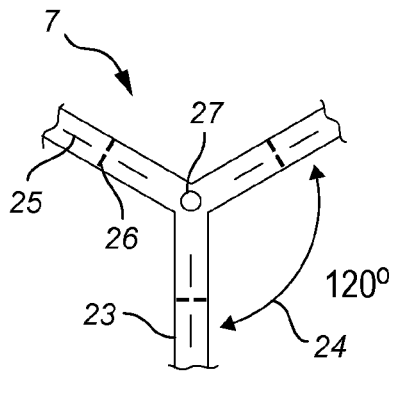
FIG. 5 consists of FIGS. 5A-5E which are illustrations of various arm based or star type carriers.

FIG. 5A shows an embodied three arm carrier 7 with spacing 24 of arms 23 about 120 degrees away from each other seed indicator lines 25 and cut lines 26 wherein it is safe for the operator to trim the carrier 7 without the risk of accidentally releasing or damaging the radioactive seed (not shown) The carrier 7 also includes a centering hole 27 for assistance when placing the carrier into a tumor bed or operative field 15.

Figure 5B:
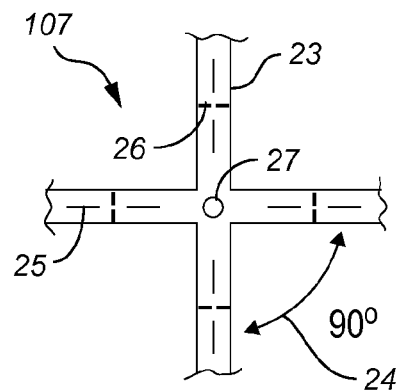

FIG. 5B shows an embodied four arm carrier 107 with spacing 24 of arms 23 about 90 degrees away from each other and the included seed indicator 25, trim lines 26 and centering hole 27 described above.

Figure 5C:
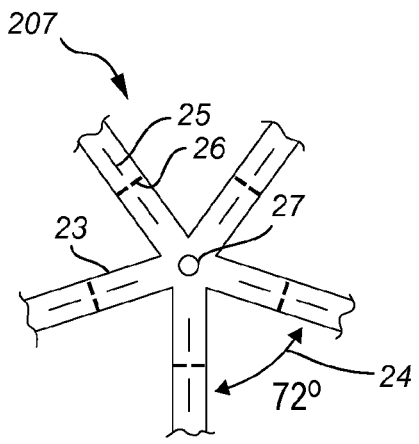

FIG. 5C shows an embodied five arm carrier 207 with spacing 24 of arms 23 about 72 degrees away from each other and the included seed indicator 25, trim lines 26 and centering hole 27 described above.

Figure 5D:
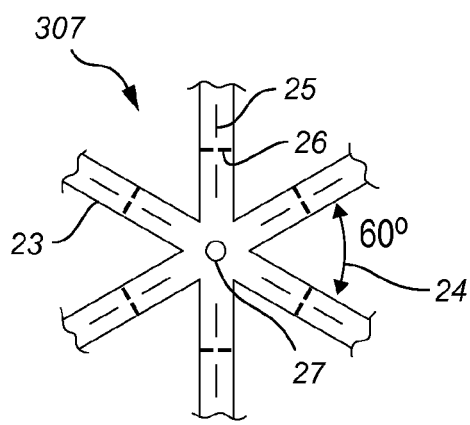

FIG. 5D shows an embodied six arm carrier 307 with spacing 24 of arms 23 about 60 degrees away from each other and the included seed indicator 25, trim lines 26 and centering hole 27 described above.

Figure 5E:
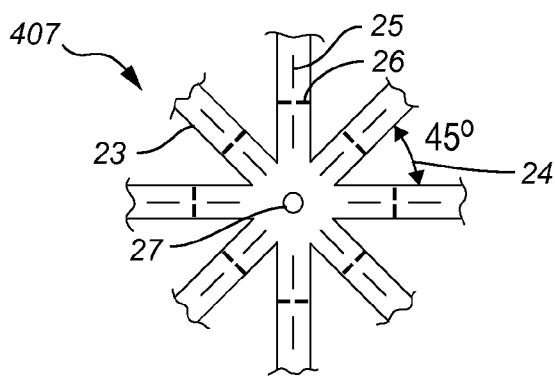

FIG. 5E shows an embodied eight arm carrier 407 with the spacing 24 of the arms 23 about 45 degrees away from each other and the included seed indicator 25, trim lines 26 and centering hole 27 described above.

Figure 7A:
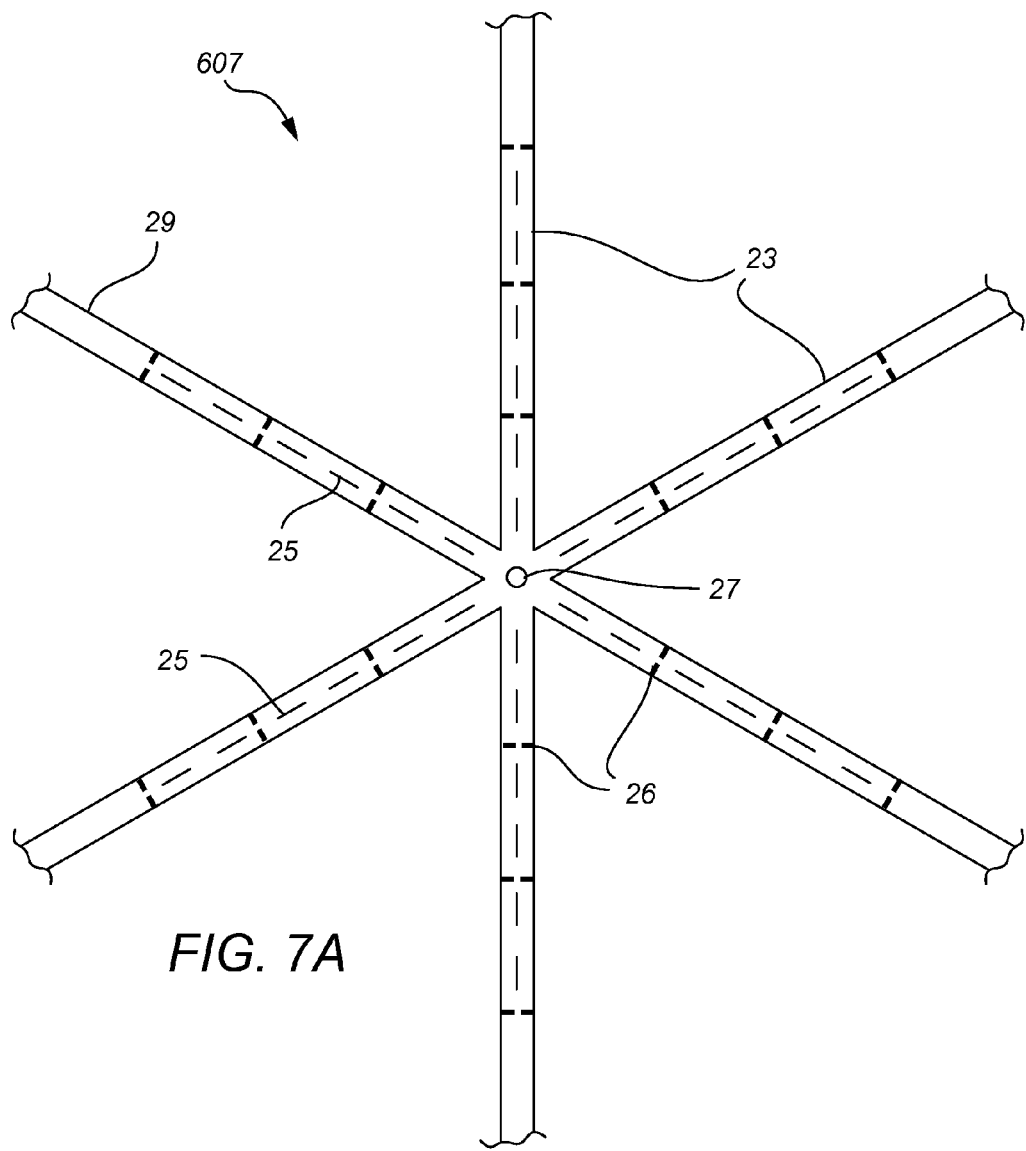
FIG. 7 is an illustration of another embodied star or arm based carrier, consisting of FIG. 7A which shows the carrier in an open position, and FIG. 7B which shows the embodied carrier in a closed loading position when attached to an endoscope for loading.

FIG. 7A is a drawing of a six arm star carrier 607 that additionally shows that the arms 23 could be trimmed along trim lines 26 to variable lengths, and the seed placement 25 within the arms may be uniform or alternated depending on the desired dosimetry and geometry required for treatment. Additionally, the carrier 607 includes a centering hole for placing the carrier on an introducer 33 and a cold tail end 29 of the arms 23 which allows the user to manipulate the placement of the arms around the introducer 33 or in the tumor bed 15.

Figure 7B:
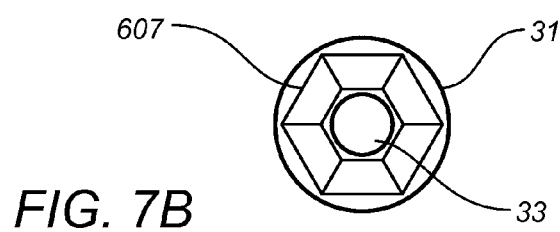

FIG. 7B shows a cross section of the six arm star 607 of FIG. 7A utilizing an endoscope 31 and draping over a unexpanded balloon catheter 33 or similar device to introduce the carrier 607 into the tumor bed 15. The arms 23 drape around the catheter 33 radially within the introducer at set distances based on the seed loading placements 25 and the number of arms 23.

Figure 8A:
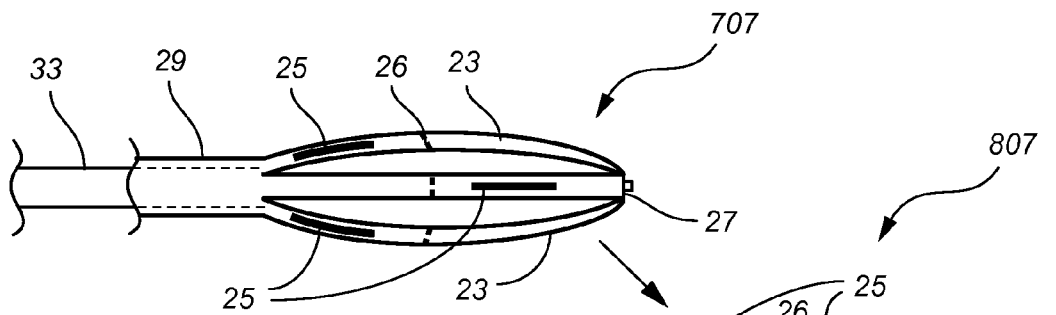
FIG. 8 consists of FIGS. 8A-8D which show an illustration of two embodied arm based carriers both expanded FIG. 8B and FIG. 8D and contracted FIG. 8A and FIG. 8C.
Figure 8B:
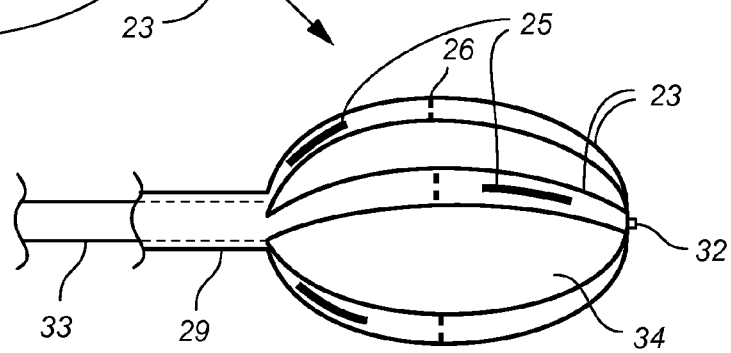

FIG. 8A shows another arm based carrier 707 in the non expanded state and FIG. 8B shows the carrier 707 in the expanded state. The carrier 707 further includes offset seed placements 25 wherein the arms 23 are around carrier balloons or expanders 34 and the seeds 25 may achieve a specific geometry in both the unexpanded and expanded positions additionally a centering nub 32 mates with the centering hole 27 of the carrier 707 and helps secure the carrier to the introducer 33, the arms 23 may be further manipulated and placed in proper position with the use of the cold tail 29.

Figure 8C:
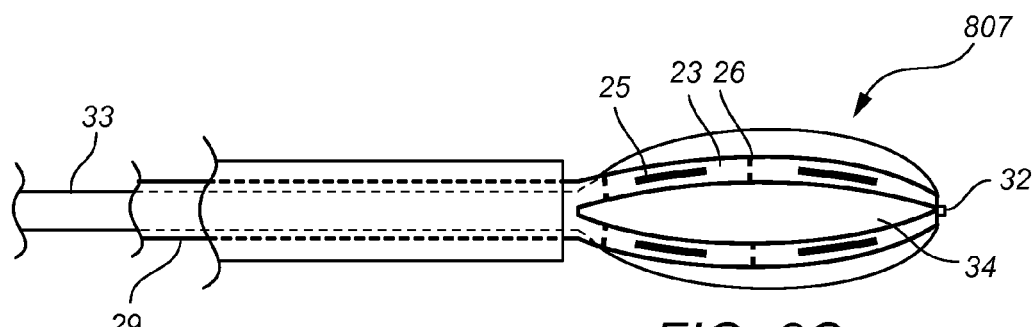
Figure 8D:
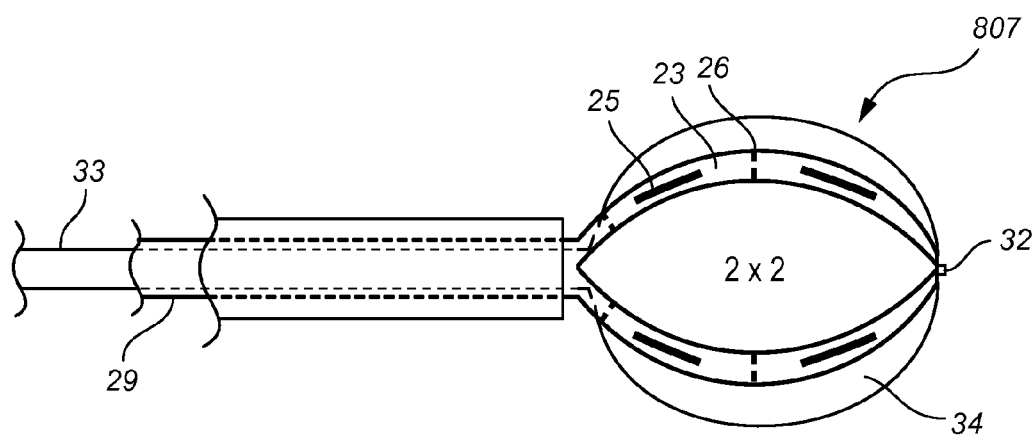

FIG. 8C shows another arm based carrier 807 in the non expanded state and FIG. 8D shows the carrier 807 in the expanded state. The carrier 807 further includes matching seed placements 25 wherein the arms 23 are around carrier balloons or expanders 34 and the seeds 25 may achieve a specific geometry in both the unexpanded and expanded positions additionally a centering nub 32 mates with the centering hole 27 of the carrier 807 and helps secure the carrier 807 to the introducer 33, the arms 23 may be further manipulated and placed in proper position with the use of the cold tail 29.

FIG. 9A and FIG. 9B shows comprise of two different arm based carriers 907 in FIG. 9A and carrier 1007 in FIG. 9B and demonstrate how an endoscope 33 or similar can be used to place a multi-arm carrier 907 or 1007 and the seeds 25 will maintain distances based on their placements on the individual arms 23.

The proportions are generally fixed by height, width and length, and set by need to maintain ideal implant geometry of seed spacing. The exact length and width depends upon the cavity size but the arm-based carrier itself may be pre made and/or pre-sized. The star or arm-based carriers additionally may have seed location presets.

The carriers of the present invention may also provide for the use of a small implantable individual carrier constructed for the localized delivery of radioactive materials such as gamma or beta irradiation or alpha particles along with radiation sensitizing agents and/or radiation damage repair inhibitors on the side(s) of the carrier(s) adjacent to the tumor.

The carriers of the present invention may also provide for the use of a small implantable individual carrier constructed for the localized delivery of radioactive materials such as gamma or beta irradiation or alpha particles with or without other radiation protection compounds on the side(s) of the carrier(s) antipodal to the radiation source and/or tissue growth promotion/healing factor compounds on the side(s) of the carrier(s) antipodal to the radiation source.

The carriers may also have differential thicknesses of the carriers themselves, wherein the carriers may range from about 2 to 6 mm thick. The seed placement in carriers of differing thicknesses may cover a range of depths for both normative placement distances and non-normative placement distances. For instance a 5 mm thick carrier may have a normative distance at 3 mm and a non-normative distance of 2 mm. If one were to have a 4 mm thick carrier with a 3 mm normative distance and 1 mm non-normative distance and another 4 mm thick carrier with a 2.5 mm normative distance and a non-normative distance, one can easily and rapidly have seed distances ranging from 1, 1.5 2, 2.5 and 3 mm just by having three different carriers ready. It is also possible to expand this range further with thicker carriers.

Stars: Problems to be solved: 1) Uniform surface dose distributions for cavities, where known dimension is a linear diameter; 2) maintaining position of sources in a uniform geometry and predictable manner once an "optimal" distribution determination is made; 3) placement within cavity/void with a minimum of additional tissue manipulation (esp. as it relates to small areas); 4) potential for adaptability to non-uniform/partially asymmetric cavities/voids; 5) rapidity of process.

GammaStars: Table 1 (all distance measurements in cm or cm2)

| Diameter | Surface Area | # Sources | Arm Length | # Sources/arm | #Arms |
|---|---|---|---|---|---|
| 1.00 | 3.1 | 3 | 1.6 | 1 | 3 |
| 1.25 | 4.9 | 4 | 1.9 | 1 | 4 |
| 1.5 | 7.1 | 6 | 2.25 | 2 | 3 |
| 1.75 | 9.6 | 9 | 2.75 | 3 | 3 |
| 1.75 | 9.6 | 8 | 2.75 | 2 | 4 |
| 2.0 | 12.6 | 15 | 3.1 | 3 | 5 |
| 2.0 | 12.6 | 12 | 3.1 | 3 | 4 |
| 2.25 | 15.9 | 15 | 3.5 | 3 | 5 |
| 2.5 | 19.6 | 20 | 3.9 | 4 | 5 |
| 2.75 | 23.8 | 24 | 4.3 | 4 | 6 |
| 3.0 | 28.3 | 24 | 4.7 | 4 | 6 |
| 3.0 | 28.3 | 30 | 4.7 | 5 | 6 |
| 3.25 | 33.2 | 30 | 5.1 | 5 | 6 |
| 3.5 | 38.5 | 36 | 5.5 | 6 | 6 |
| 3.5 | 38.5 | 35 | 5.5 | 5 | 7 |
| 3.75 | 44.2 | 42 | 5.9 | 7 | 7 |
| 3.75 | 44.2 | 40 | 5.9 | 5 | 8 |
| 4.0 | 50.3 | 48 | 6.3 | 6 | 8 |
| 4.0 | 50.3 | 49 | 6.3 | 7 | 7 |
| 4.25 | 56.7 | 56 | 6.7 | 7 | 8 |
| 4.5 | 63.6 | 64 | 7.0 | 8 | 8 |
| 4.75 | 70.9 | 64 | 7.5 | 8 | 8 |
| 5.0 | 78.5 | 72 | 7.8 | 9 | 8 |

Table 1, column 1: lists diameters of some commonly encountered surgical cavities.

Table 1, column 2: relates diameter of sphere to surface area of sphere of this diameter (4piR2).

Table 1, column 3: relates surface area to the number of sources needed, assuming 1 source per cm2 of surface area.

Table 1, column 4: relates possible star "arm" length for given cavity (circumference/2).

Table 1, column 5: relates possible number of sources per arm, at a spacing of ~1 per linear cm.

Table 1, column 6: relates possible number(s) of arms on a star that are needed to treat surface area from column 2 at ~1 source/cm2 of surface area with a uniform geometry.

Star Selection Process:

1) Determine cavity/void diameter (Sound, ultrasound, CT, MRI or visually) (Table 1, column 1)

2) From diameter, determine surface area in cm2 (Table 1, column 2)

3) Using ~1 source per cm2 area, determine the number of sources needed (Table 1, column 3)

4) Star selection (how many arms) (Table 1, column 4) is made on the number of sources needed overall, with the approximation of 1 source per cm along radial length of arm Table 1, column 5 and column 6) for a given diameter. As shown in Table 1, column 3 sometimes multiple combinations result and would be similarly efficacious.

Star insertion Process:

A) Over Guide:

1) Choose star as above 2) slide star over guide with tip of guide in centering hole/depression at closed end of star (intersection of arms) 3) insert to desired position in cavity/void, trimming arm or arm excess as needed 4) withdraw guide 5) position, pack open, suture, glue or otherwise secure star to side of cavity/void.

B) Over Expandable Catheter:

1) Choose star as above 2) position Star over appropriate catheter with centering tip (FIG. 3 new) such that tip end of catheter extends to closed end of Star and cold tail is just beyond the expansion area of catheter 3) insert to desired position in cavity/void, trimming arm or arms as needed 4) expand catheter to desired characteristics 5) collapse catheter 6) withdraw catheter 7) position, pack open, suture, glue or otherwise secure star to side of cavity/void.

C) Via Endoscope or Similar with Expanding Catheter:

1) Choose star as above 2) position Star over appropriate catheter with centering tip such that tip end of catheter extends to closed end of Star and cold tail is just beyond the expansion area of catheter (FIG. 4 new) 3) insert to desired position in endoscope or introducer, trimming arm or arms as needed 4) insert endoscope or introducer to desired position in cavity/void 5) withdraw endoscope or further catheter with centering tip such that in either case the catheter introducer/star apparatus is in desired location and cold tail remains within endoscope 6) expand catheter to desired characteristics 7) collapse catheter 8) withdraw catheter 9) position, pack open, suture, glue or otherwise secure star to side of cavity/void 10) withdraw endoscope. It is recognized that variations in this technique are likely to arise.

Arm-Based Flower Petal Style Carrier Embodiment

Figure 6:
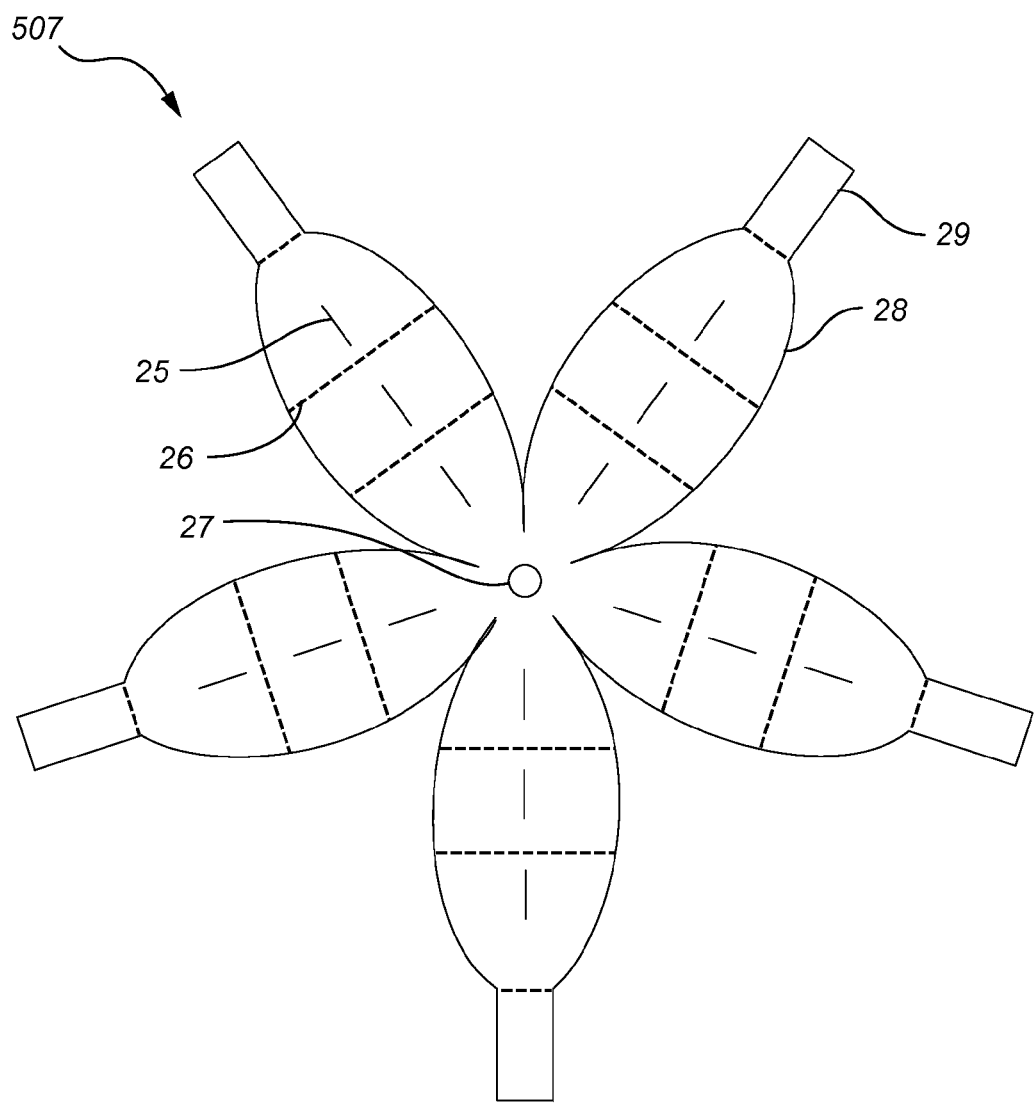
FIG. 6 is an illustration of a arm-based carrier system further including petal type arms.

FIG. 6 shows an embodied arm based carrier 507, wherein the petal arms 28 are thicker and more like petal structures than the arms 23 of the carriers shown in FIG. 5. The broader petal arms 28 embodied in the Petal style carrier 507 allow for greater spacing control between carrier arms 28 and structural support. Additionally, the petal style arms 28 may be constructed to facilitate the localized delivery of radioactive materials such as gamma or beta irradiation or alpha particles along with chemotherapy agents or tumoricidal/targeted/immunotherapeutic, viral/viral vector agent(s), radiation sensitizing agents and/or radiation damage repair inhibitors; on the side(s) of the carrier(s) adjacent to the tumor and/or radiation protection compounds on the side(s) of the carrier(s) antipodal to the radiation source and/or tissue growth promotion/healing factor compounds on the side(s) of the carrier(s) antipodal to the radiation source.

The petal based carrier 507 of FIG. 6 can be customized along the various trim lines 26, or have arms 28 removed based on the limitations of the operative field. The petal based carrier also includes seed indicator lines 25 and a centering hole 27 for assistance when placing.

Combination of Dots and Arm-Based or Star Style Carriers Embodiment

As shown in FIG. 10 it is possible to combine an arm based carrier 907 and a plurality of different dot sized carriers 2 to create a carrier system for filling a tumor bed and maintaining a precise dosimetry. The combination carrier system may be placed with an introducer or catheter 33 into a tumor bed or operative field 15. The arms 23 of the arm based carrier 907 have space between which is filled with hot dot carrier 2 of different sizes.

Although the invention has been described with reference to the above examples, it will be understood that modifications and variations are encompassed within the spirit and scope of the invention. Accordingly, the invention is limited only by the following claims.

What is claimed is:

1. A treatment system comprising:
an introducer comprising a mating tip sized to engage with a radioactive seed carrier to maintain position of the radioactive seed carrier with reference to the introducer as the radioactive seed carrier is inserted into a cavity of a mammal, wherein the introducer is removable from the radioactive seed carrier;
the radioactive seed carrier comprising:
a central portion having an aperture configured to receive the mating tip of the introducer;
a plurality of elongate members each having:
a proximal end coupled to the central portion;
a distal end; and
a carrier portion between the proximal end and the distal end, the carrier portion embedding one or more radioactive seeds in a spaced relationship;
wherein the radioactive seed carrier comprises
a collapsed state wherein each of the plurality of elongate members are substantially parallel to one another about a central elongate axis between the plurality of elongate members; and
an expanded state wherein each of the plurality of elongate members are flexed outward from the central elongate axis about a central portion of respective elongate members;
wherein the introducer is adapted for removal from the radioactive seed carrier.

2. The treatment system of claim 1, wherein the introducer comprises a catheter having a balloon adapted for insertion into the cavity of a mammal to which radioactive therapy is prescribed, wherein the balloon has an inflated state wherein volume of the balloon is greater than in a deflated state, the balloon being adapted for placement in the cavity of the mammal in the deflated state and inflation to the inflated state when in the cavity.

3. The treatment system of claim 1, wherein the radioactive seed carrier is adapted to retain the expanded state within the cavity of the mammal after the introducer is removed from within the radioactive seed carrier.

4. The treatment system of claim 1, wherein the introducer comprises an endoscope.

5. A method comprising:
determining a carrier configuration based on a radiation therapy plan, the carrier configuration indicating at least:
an arm quantity of elongate arms, the arm quantity being at least three; and
a seed quantity of radioactive seeds for each of the elongate arms, the seed quantity being at least one;
preparing a radioactive seed carrier having a plurality of elongate arms and a plurality of radioactive seeds matching the determined carrier configuration embedded therein;
engaging a mating tip of an introduction device with a mating aperture of the radioactive seed carrier;
with the introduction device mated to the radioactive seed carrier, moving the introduction device so that the radioactive seed carrier is within a cavity of a mammal; and
withdrawing the introduction device, leaving the radioactive seed carrier within the cavity of the mammal.

6. The method of claim 5, further comprising:
trimming a first elongate arm of the plurality of elongate arms to shorten length of the first elongate arm.

7. The method of claim 6, wherein the first elongate arm includes one or more visible trim lines identifying portions of the first elongate arm where no radioactive seeds are embedded.

8. A method comprising:
positioning a radioactive seed carrier for engagement with an introduction device, the radioactive seed carrier having a plurality of elongate arms, each of the plurality of elongate arms having one or more radioactive seeds embedded therein;
engaging a mating tip of the introduction device with a mating aperture of the radioactive seed carrier;
moving the introduction device to insert the radioactive seed carrier within a cavity of a mammal; and
withdrawing the introduction device, leaving the radioactive seed carrier within the cavity of the mammal.

9. The method of claim 8, further comprising:
causing a portion of the introduction device within the radioactive seed carrier to expand, thereby expanding at least some of the elongate arms within the cavity of the mammal.

10. The method of claim 8, further comprising:
receiving, from a provider, the radioactive seed carrier with radioactive seeds embedded therein.

11. The method of claim 8, further comprising:
determining a quantity of elongate arms, the arm quantity being at least three; and
preparing the radioactive seed carrier, wherein the plurality of elongate arms is the determined quantity.

* * * * *